United States Patent [19]
Fenton

[11] Patent Number: 5,499,633
[45] Date of Patent: Mar. 19, 1996

[54] ANTI-SNORING DEVICE WITH ADJUSTABLE UPPER AND LOWER RELATIONAL MEMBERS

[76] Inventor: Douglas F. Fenton, 2559 Union St., San Francisco, Calif. 94123

[21] Appl. No.: 218,714

[22] Filed: Mar. 28, 1994

Related U.S. Application Data

[63] Continuation-in-part of Ser. No. 168,844, Dec. 17, 1993, abandoned.

[51] Int. Cl.$^6$ ............................... A61F 5/56; A61C 5/14
[52] U.S. Cl. ............................... 128/848; 128/859; 433/6
[58] Field of Search ............................ 433/6; 128/848, 128/859, 861, 862

[56] References Cited

U.S. PATENT DOCUMENTS

| | | | |
|---|---|---|---|
| 1,674,336 | 6/1928 | King. | |
| 3,132,647 | 5/1964 | Corniello | 128/136 |
| 3,434,470 | 3/1969 | Strickland | 128/136 |
| 4,169,473 | 10/1979 | Samelson | 128/136 |
| 4,505,672 | 3/1985 | Kurz | 433/6 |
| 4,715,367 | 12/1987 | Crossley | 128/136 |
| 4,901,737 | 2/1990 | Toone | 128/848 |
| 5,062,422 | 11/1991 | Kinkade | 128/207.14 |
| 5,092,346 | 3/1992 | Hays et al. | 128/848 |
| 5,267,862 | 12/1993 | Parker | 433/215 |
| 5,313,960 | 5/1994 | Tomasi | 128/848 |
| 5,365,945 | 11/1994 | Halstrom | 128/848 |

FOREIGN PATENT DOCUMENTS

| | | | |
|---|---|---|---|
| 0359135 | 3/1990 | European Pat. Off. | 128/859 |
| 2320501 | 11/1974 | Germany | 128/848 |

OTHER PUBLICATIONS

Lowe, "Dental Appliances for the Treatment of Snoring and OSA", Principles and Practice of Sleep Medicine, 2nd Edn., Kryger et al., Eds. pp. 722–735.

Primary Examiner—Robert A. Hafer
Assistant Examiner—Michael O'Neill
Attorney, Agent, or Firm—Virginia H. Meyer

[57] ABSTRACT

An adjustable oral device for placement within the mouth of a user to reduce or eliminate snoring. The device comprises an upper member having a substantially curved shape and defining an upwardly oriented channel for receiving at least some of the upper teeth of a user; a lower member having a substantially curved shape and defining a downwardly oriented channel for receiving at least some of the lower teeth of a user; wherein the upper member is adjustably coupled by the user to the lower member in a spaced relationship such that the lower member is positioned relative to the upper member so that when the user's teeth are retained within the device, the user's lower jaw is biased substantially forward of its normal biting or resting position to reduce snoring. The device can include an anterior tongue space between the upper and lower members, and can further include moldable material positioned within at least one of the channels for substantially conforming to a shape of the teeth, thus allowing the device to be customized for individual users.

16 Claims, 3 Drawing Sheets

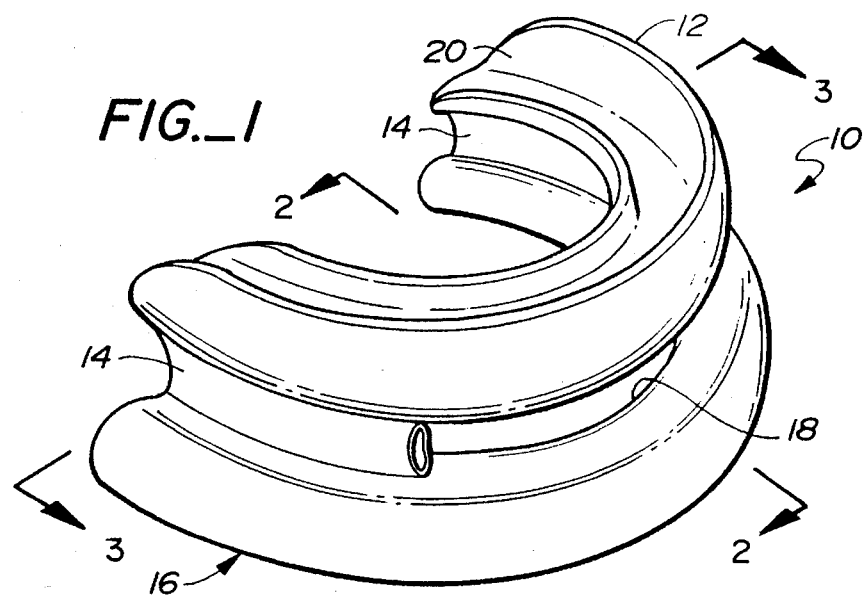
FIG._1
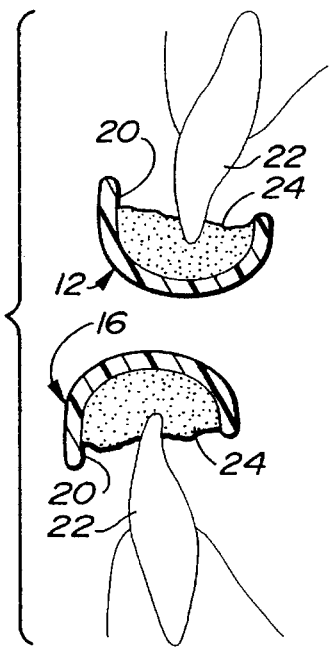
FIG._2
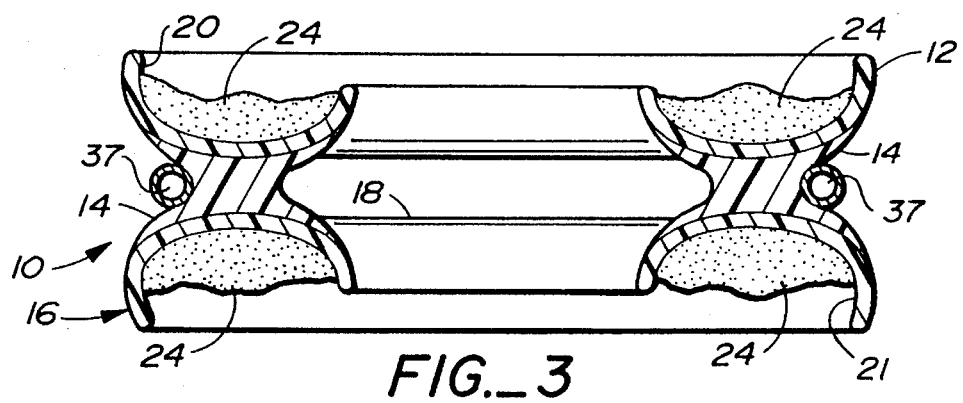
FIG._3

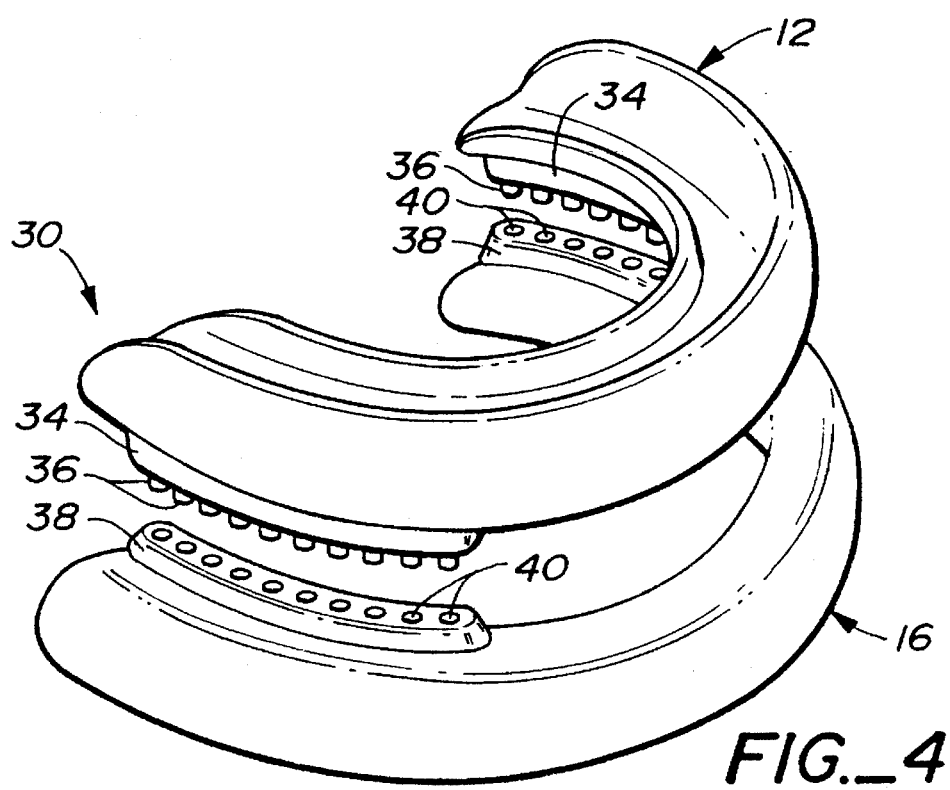
FIG._4
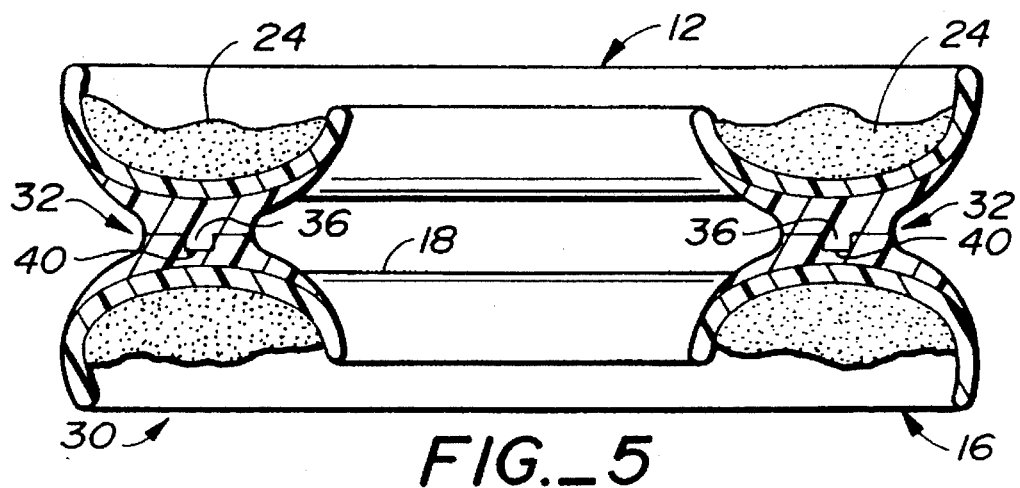
FIG._5

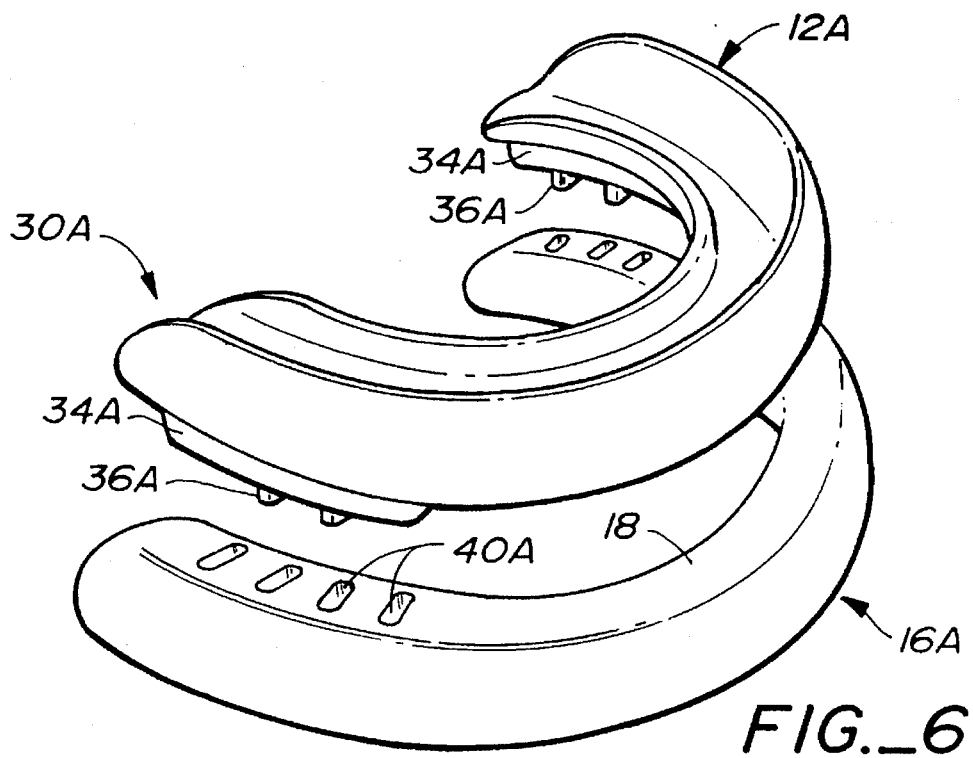
FIG._6
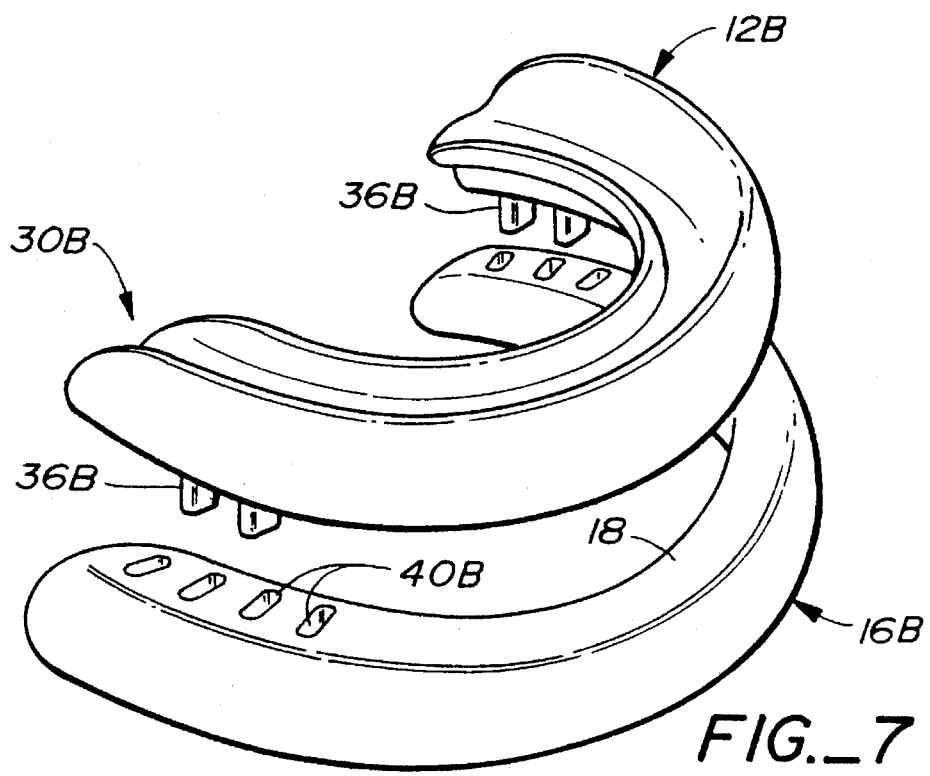
FIG._7

ANTI-SNORING DEVICE WITH ADJUSTABLE UPPER AND LOWER RELATIONAL MEMBERS

CROSS-REFERENCE

The present application is a continuation-in-part of U.S. Ser. No. 08/168,844 filed Dec. 17, 1993, now abandoned.

FIELD OF THE INVENTION

The present invention relates generally to snore reducing devices and more particularly to an anti-snore dental device for placement within the mouth of a user to reduce or eliminate snoring.

BACKGROUND OF THE INVENTION

Most snoring is caused by a reduction of the free flow of air through the passages at the back of the mouth and nose. This is the collapsible part of the airway where the tongue and upper throat meet the soft palate and uvula. During waking hours, normal muscle tone in most individuals maintains the tissues in these areas in adequate spacial relationships so air can flow freely through the passages at the back of the mouth and nose. However, during periods of sleep, some muscle tone is lost. This loss of muscle tone can cause partial blockage of the passages at the back of the mouth and nose, especially as the result of a backward relaxation of the tongue during sleep. In some individuals, this blockage is significant enough to allow the uvula and soft palate at the back of the mouth to strike against each other and vibrate during breathing. The snoring noise is created as a result of this vibration.

A number of prior patents disclose that snoring can be reduced, if not altogether prevented, by providing for unobstructed air flow between the tongue and the soft palate.

For example, U.S. Pat. No. 1,674,336 to King teaches a respirator for placement between the teeth of the user, for preventing snoring and for facilitating breathing. The King device resembles an athletic mouth guard, and has upper and lower channels which receive the upper and lower teeth, respectively. The channels are spaced apart so there is a central air passage between them. In use, the King device moves the lower jaw downward, not forward. King claims movement of the lower jaw downward opens the posterior airway to facilitate the passage of air to and from the lungs.

U.S. Pat. No. 3,132,647 to Corniello teaches keeping the air passage open by engaging and depressing the rear portion of the tongue while supporting a portion of the downwardly hanging soft palate. The Corniello device resembles the upper portion of an athletic mouth guard, with a metal tongue depressor at the back.

U.S. Pat. No. 4,169,473 to Samelson describes an anti-snoring and anti-bruxism device for positioning within the mouth of a user to prevent snoring and nocturnal tooth grinding. The Samelson device has an integrally molded body providing dental engaging arches and a rearwardly-opening central socket for cooperating with the forward portion of the user's tongue in a manner which draws the tongue forwardly in order to increase the unobstructed dimension of the nasal breathing passage. The Samelson device substantially eliminates oral breathing and allows the tongue to be held in the socket by a negative pressure developed therein.

U.S. Pat. No. 4,901,737 to Toone discloses another anti-snoring device. The Toone device repositions the mandible in an inferior (open) and anterior (protrusive) position, as compared to the normally closed position of the jaw, in order to improve airway patency. The Toone device is a rigid, generally V-shaped wedge molded to the entire patient's upper mandibular and a portion of the maxillary dentations. In use, wire grips hold the appliance to the upper teeth.

U.S. Pat. No. 5,092,346 to Hayes and Meade discloses a dental orthosis having an upper portion designed to receive the upper teeth of the user, and a lower ramp structure whereby natural jaw motions are alleged to encourage engagement of the user's lower teeth against the ramp, which is claimed to move the lower jaw into a more forward position. An aperture in the Hayes and Meade facilitates the passage of air for mouth breathing. By inducing the lower jaw to a more forward position, the device claims to induce a more open posterior airway in the user, resulting in a reduction in snoring.

While these devices may fulfill their respective objectives and requirements, they suffer from being cumbersome to wear, and from the fact that they must be fitted by a dentist or dental professional.

There is a need for an anti-snoring device that facilitates unobstructed air flow between the tongue and the soft palate and yet is comfortable to wear. Such a device should be simple in design so it can be manufactured and sold at low cost. To further help reduce costs, such a device should not require fitting by a dental professional.

Therefore it is an object of this invention to provide an oral anti-snoring device that facilitates unobstructed air flow between the tongue and the soft palate, and the rear of the throat.

Another object of the invention is to provide a device of the type described which is of durable and reliable construction.

Another object of the invention is to provide a device which is easy and inexpensive to produce from sanitary materials, thus rendering it usable over and over again.

Another object of the invention is to provide a device of the type described which does not cause discomfort to the user or harm to the teeth or gums during use.

Another object of the invention is to provide a device of the type described which includes means for custom firing the device to an individual user, in ways which allow the device to be self-fitted by anyone with a snoring problem, without the need for a dental professional.

Still another object of the invention is to provide a device of the type described which includes means for custom fitting the device to an individual user, such that the user can make his or her own corrections in positions of the mandible as needed or desired.

Other objects of the invention will become apparent from the following description and the drawings.

BRIEF SUMMARY OF THE INVENTION

The invention is an anti-snoring device which is insertable in, and removable from, the mouth by the user, who uses the device during periods of sleep to alleviate, reduce or eliminate snoring. The device comprises an upper member for receiving upper teeth of the user, which is joined in a spaced relationship to a lower member for receiving lower teeth of the user. The lower member is selectively positioned with respect to the upper member such that the lower member, by receiving the lower teeth of the user, moves the lower jaw of the user to a position that is forward of its "normal" resting or biting position. This forward movement of the lower jaw significantly opens the airway of the user, thereby alleviating, reducing, or eliminating snoring. In addition, a passage is preferably provided between the members to create space for anterior movement of the tongue during use. This anterior movement of the tongue also aids in opening the airway of the user, thereby further reducing snoring. The device of the invention may include moldable means which allow the device to be made to conform to the teeth arrangement of a particular user. Further, according to the teaching of the invention, the upper and lower members of the anti-snoring device may be fixedly joined to one another in a spaced relationship, preferably such that the lower member is positioned anteriorly of the upper member. Alternatively the device may include connectors for adjustably joining the upper member to the lower member in a spaced relationship such that the lower member, when it has received at least some of the lower teeth of the user, will force the lower jaw of the user into a position that is substantially forward of the normal biting or resting position of the user. This adjustable embodiment of the invention further allows the device to be customized to conform to the jaw arrangement of a particular user.

DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of a first embodiment of an anti-snore dental device comprising the present invention, showing the upper and lower members fixedly mounted to one another.

FIG. 2 is a cross sectional view taken along line 2—2 of FIG. 1.

FIG. 3 is a further cross sectional view taken along line 3—3 of FIG. 1.

FIG. 4 is a perspective view, partially exploded, of a second embodiment of an anti-snore dental device comprising the present invention, showing adjustable coupling between the upper and lower members.

FIG. 5 is a cross sectional view of a second embodiment detailing adjustable coupling between the upper and lower members.

FIG. 6 is a perspective view, partially exploded, of a third embodiment of an anti-snore dental device comprising the present invention, showing another version of adjustable coupling between the upper and lower members.

FIG. 7 is a perspective view, partially exploded, of a fourth embodiment of an anti-snore dental device comprising the present invention, showing yet another version of adjustable coupling between the upper and lower members.

DETAILED DESCRIPTION OF THE INVENTION

With reference now to the drawings, and in particular to FIGS. 1–3 thereof, a first embodiment of a new anti-snore dental device embodying the principles and concepts of the present invention and generally designated by the reference numeral 10 will be described.

From an overview standpoint, anti-snore dental device 10 comprises an upper member 12 for receiving the upper teeth of a user. In one embodiment, integrally or otherwise fixedly secured to upper member 12 is a pair of stanchions 14 which fixedly couple upper member 12 in a substantially parallel, spaced relationship to lower member 16, as best illustrated in FIG. 1. Stanchions 14 are positioned on opposed sides of members 12, 16 so as to define a tongue space 18 between members 12 and 16. Tongue space 18 allows more forward movement of the tongue, which further opens the airway of the user, and thus helps to reduce snoring. In addition, the tongue space makes the device more comfortable to use. In a preferred form, stanchions 14 are tapered so that air can pass between the cheek side of the stanchions and the cheek, to enable the user to orally breath while using the device 10. If the user is unable to breath through his or her nose, a plastic or rubber tube 37 may be attached by non-toxic means to the cheek side of one or both stanchions to assure an open airway for users who must breath through their mouth.

Members 12, 16 are coupled together, either fixedly as shown in FIGS. 1–3, or adjustably as will later be described. When upper member 12 is fixedly attached to lower member 16, lower member 16 is preferably positioned substantially anteriorly (or substantially forward) of upper member 12, thereby positioning the lower jaw of the user into a more forward position to alleviate, reduce, or eliminate snoring by significantly opening the airway of the user. Alternatively, as shown in FIGS. 4–7, members 12, 15 are adjustably coupled together. In adjustable form, lower member 16 is selectively positioned with respect to upper member 12 such that lower member 16, by receiving the lower teeth of the user, moves the lower jaw of the user to a position that is substantially forward of its "normal" biting or resting position. In most instances this will require that lower member 12 be positioned substantially anteriorly to upper member 16. However, it is important to realize that it is the lower jaw of the user which must be positioned so that it is substantially forward of its normal resting or biting position. Some users will not be able to position their lower jaws substantially forward of their upper jaws, but will still be able to position their lower jaws substantially forward of their lower jaw's normal resting or biting position. The adjustable embodiment of the device of the present invention is especially useful for these individuals, or other users who want to customize the device for their particular jaw configurations.

As used herein, in both the specification and the claims, substantially anterior, or substantially forward, means that lower member 16 will be positioned from about 1 to about 10 mm, and preferably from about 2 to about 6 mm, forward of the position of upper member 12, or that lower member 16 will be positioned in such a way that, when at least some of the lower teeth of the user are engaged in lower channel 21, the lower jaw of the user will be forced forward, from about 1 to about 10 mm, and preferably from about 2 to about 6 mm, of its normal resting or biting position. Again, this forward movement of the lower jaw significantly opens the airway of the user, thereby alleviating, reducing, or eliminating snoring. Additionally, when the lower jaw is moved to a more forward position, because of its attachment to the inside of the mandible forming a part of the lower jaw, the tongue is also biased into more forward position, thereby substantially reducing the interference and vibrations caused by a relaxation of the lower jaw and tongue during sleep.

In use, anti-snore dental device 10 may be comfortably positioned within the mouth of a user, thereby automatically retaining the user's lower jaw in a more forward position. By substantially increasing the opening of the airway of the user, the volume of air flowing therethrough is correspondingly increased while the velocity of air is reduced, resulting in a reduction or elimination of vibration of the soft palate, uvula, and surrounding soft tissues.

More specifically, anti-snore dental device 10 comprises a substantially U-shaped upper member 12 configured to receive upper teeth of a user. Upper member 12 is formed to define a channel 20 into which teeth 22 of a user may be received, as best illustrated in FIG. 2. Similarly, device 10 includes a substantially U-shaped lower member 16 configured to receive lower teeth of a user within a channel 21 formed therein. Upper and lower members 12, 16 may be constructed from a wide variety of materials, but are preferably comprised of a soft, semi-rigid, substantially resilient plastic which is comfortable to the soft tissues present within a user's mouth. Suitable plastics will have good physical characteristics and preferably will have a specific gravity of about 1.20, a tensile strength (yield) of about 9000 and a softening temperature of about 310 degrees F. Such suitable plastics are used to provide a framework for the device. An example of a preferred suitable plastic for providing a framework for the device of the present invention is the resilient semi-rigid polycarbonate resin sold by the General Electric Company under the Registered Trademark LEXAN.

The material used to provide a framework for the device may be used in conjunction with additional moldable materials 24, as discussed further below.

In a preferred form, either or both of upper and lower members 12, 16 may be provided with a moldable material 24 positioned within the channels 20, 21 thereof, as best illustrated in FIGS. 2 and 3. The moldable material 24 may comprise a resilient material, such as soft rubber or foam, a replaceable wax, or a moldable resin, such as an acetate copolymer resin, an ethylene-vinyl acetate copolymer resin, polyethers, polysulfides, condensation silicones, hydrophilic addition silicones, light cured elastomers, polyvinylsiloxane materials, or hydromonophase vinyl polysiloxanes.

For example, when the device is formed from polycarbonate resin-thermoplastic having a layer of acetate copolymer resin bonded thereto at the teeth-engaging surfaces, namely the channels within the upper and lower members which receive the upper and lower teeth, individual fitting of the device to the user is greatly simplified. In this embodiment the acetate copolymer resin layer is preferably about 3 to 4 millimeters in thickness in the channels. A suitable acetate copolymer resin has a substantially lower softening and molding temperature than that of polycarbonate materials used to make the rest of the device, e.g., upper and lower members 12, 16, thereby allowing the device 10 to be heated and subsequently inserted into a user's mouth such that an engagement of the user's teeth 22 to the moldable material 24 will create a customized fit of the device 10 to that particular user. A softening temperature of about 140–150 degrees F. is especially suitable for moldable material positioned with the channels. An example of a suitable copolymer resin for use in the present invention is sold by the Du Pont Company under the Registered Trademark ELVAX.

When the device is formed from polycarbonate resin-thermoplastic having a layer of acetate copolymer resin bonded thereto at the teeth-engaging surfaces, custom fitting of the device a user's mouth is simplified. For example, immersion of the device in a hot fluid, preferably water, prior to the fitting serves to impart a yielding nature to the acetate copolymer resin layer whereby it accepts the user's distinctive tooth configuration during the fitting process. Once the acetate copolymer resin is sufficiently moldable, the device is forcibly inserted against the user's upper and lower jaws and teeth. Upon cooling to ambient temperature, the acetate copolymer resin retains the user's tooth configuration, for ease of repeat placement by the user. Excess resin can be cut from the device to make the device more comfortable in use. This reduces the time and cost of fitting the device. There is no need for the use of molds or employing the services of dental laboratories. The device can be fitted to the user by the user.

As indicated above, other moldable materials, such as dental wax, can be utilized with the device of the invention. When dental wax is utilized as the moldable material 24, the wax may be softened by immersing it in hot fluid, such as hot water from the faucet. When the wax is soft, it is pressed into channel(s) 20, 21 after which, while the wax is still soft, the device is forcibly inserted against the user's upper and lower jaws and teeth, as described above for the acetate copolymer resin. An advantage of using the dental wax is that the wax may be removed easily to clean the device, or to remold the device to the teeth of the user or to easily change the jaw position for comfort. This may be desirable if the user is undergoing dental work, or has trouble maintaining a particular position.

When wax is used with the device, small holes, indentations or roughened areas (not shown in the drawings) may be made in the channels to help anchor the wax.

An example of suitable dental wax for use with the device of the present invention is dental sold by the Hygenic Company under the Trademark Pink Base Plate Wax.

Dental wax and moldable resins are available separately, or can be packaged and sold with the anti-snoring device in kit form.

Returning now to a more general discussion of the device of the invention, in one embodiment upper and lower members 12, 16 are integrally or otherwise connected by a pair of stanchions 14 which extend therebetween to position the members in a substantially spaced, parallel relationship. As best illustrated in FIG. 2, lower member 16 is preferably positioned slightly forward of upper member 12. This arrangement substantially positions the lower jaw into a more forward position, whereby snoring is reduced or eliminated through the resulting opening of the user's airway. While it will be apparent that the amount of forward positioning of the lower jaw which may be required or desired to alleviate snoring in any particular individual will depend on the configuration of that individual's jaw, it is to be noted that relatively minor forward movement of the lower jaw, for example in the range of 1 to 10 mm, serves to reduce the incidence of snoring. Accordingly, the devices of the invention may be made in a number of "standard sizes", whereby an individual could choose the size that best fit the configuration of his or her particular jaw. Alternatively, as was discussed above and will be discussed in more detail below, the invention teaches additional embodiments of the anti-snoring device whereby adjustable connectors are used to selectively position upper and lower members 12, 16 together in a spaced relationship such that lower member 16 is positioned so that it forces the lower jaw of the user into a position that is substantially anterior of the jaw's normal resting or biting position. This adjustable embodiment enables the anti-snoring device to be easily "customized" to accommodate the jaws of individual users. Furthermore, the use of a moldable material allows further variation in the extent of forward movement of the jaw. When the moldable means are dental wax or moldable resin, corrections can easily be made by the user if the device is either uncomfortable or the lower jaw needs to be moved for more effectiveness.

The anti-snoring device of the present invention will preferably have a an anterior passage between the upper and lower members. This passage is shown with reference number 18 in the drawings. When desired, stanchion(s) 14 may be positioned on respectively opposed sides of members 12 and/or 16 and spaced apart to define passage 18 between both the members and the stanchions. Alternatively adjustable connectors may be used to define passage 18. Passage 18 allows the tongue to move anteriorly between the upper and lower members. This creates more space for air in the posterior area.

In use, the anti-snore dental device 10 may be comfortably positioned within the mouth of a user, thereby to automatically retain the user's lower jaw in a more forward position. By substantially increasing the opening of the airway of the user, the volume of air flowing therethrough is correspondingly increased, while the velocity is decreased, resulting in a reduction or elimination of vibration of the soft palate, uvula, and surrounding soft tissues.

A second embodiment of the present invention, as generally designated by the reference numeral 30, which comprises substantially all of the features and structure of the foregoing embodiment 10 and which further comprises adjustable connectors, will now be described. As best shown in FIGS. 4–7, adjustable connectors, such as those shown as 32 in the FIG. 5, can be used to allow a user to selectively position upper and lower members 12, 16 together. For example, in second embodiment 30, (as shown in FIGS. 4 and 5) upper member 12 is provided with a pair of upper stanchions 34 which have a plurality of downwardly facing projections 36 extending therefrom. Lower member 16 is provided with a pair of lower stanchions 38 of substantially similar shape to those of the upper stanchions 34, but having a plurality of apertures 40 operable to receive the projections 36 extending from upper stanchions 34, as best illustrated in FIG. 4. This structure maintains tongue space 18 while allowing lower member 16 to be selectively latitudinally positioned with respect to upper member 12. Alternatively, lower member 16 could have stanchions and a plurality of upwardly facing projections extending therefrom, and upper member 12 could have stanchions with a plurality of apertures therein operable to receive the projections extending from lower member 16.

FIG. 5 is a cross sectional view of second embodiment 30. It can be seen from this Figure that projections 36, projecting from each of upper stanchions 34, each define a proximal end having a first diameter which is slightly smaller than a second diameter of a distal end thereof. Similarly, apertures 40 are shaped so as to define a top end having a diameter equal to the first diameter of the projections 36 as described above, and a further diameter located at a bottom end thereof equal the second diameter of the projections 36. Such arrangement allows the projections to be snapped into the apertures 40, thereby retaining upper and lower members 12, 16 together, while also providing for selectively adjustable longitudinal positioning of the members by a user. More specifically, any of the plurality of projections 36 may be engaged as described above into any of the plurality of apertures, with unused projections or apertures remaining uncoupled, to couple stanchions 34, 38 securely together. By this structure, a user may adjust lower member 16 into a desired anterior position with respect to upper member 12, thereby positioning the lower jaw into any forward position selected by such user.

The adjustable aspect of positioning lower member 16 so the lower jaw of the user is forced into a position that is anterior with respect to the lower jaw's normal resting or biting position is further illustrated in FIGS. 6 and 7. FIG. 6 shows a third embodiment of the present invention, as generally designated by the reference numeral 30A. This embodiment comprises substantially all of the features and structures of embodiment 10 and further comprises adjustable connectors wherein upper member 12A is provided with a pair of upper stanchions 34A which have a plurality of downwardly facing projections 36A extending therefrom. However, in embodiment three, unlike embodiment two, lower member 12A has no stanchions per se, but instead has sufficient thickness to allow a plurality of apertures 40A to be placed directly therein. Apertures 40A are designed and positioned to engage projections 36A, thereby securing upper member 12A and lower member 16A together, while still maintaining tongue space 18. Alternatively, lower member 16A could have stanchions and a plurality of upwardly facing projections extending therefrom, and upper member 12A could have a plurality of apertures placed directly therein (not shown).

FIG. 7 shows a fourth embodiment of the present invention, as generally designated by the reference numeral 30B. In this embodiment, a plurality of downwardly facing projections 36B extend directly from upper member 12B, and lower member 16B has a plurality of apertures 40B placed directly therein. Projections 36B are of sufficient length so that when projections 36B are engaged by apertures 40B, tongue space 18 is maintained between upper member 12B and lower member 16B. Again, lower member 16B could have a plurality of upwardly facing projections extending therefrom, and upper member 12B could have a plurality of apertures placed directly therein (not shown).

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. An anti-snore dental device comprising:

an upper member having a substantially curved shape and defining an upwardly oriented channel for receiving at least a portion of at least some of the upper teeth of a user, the upper member further defining opposed sides thereof;

a lower member having a substantially curved shaped and defining a downwardly oriented channel for receiving at least a portion of at least some of the lower teeth of a user, the lower member further defining opposed sides thereof;

adjustable connectors for adjustably joining the upper and lower members together wherein the adjustable connectors comprise a pair of upper stanchions each coupled to one of the opposed sides of the upper member, the upper stanchions each having at least two projections extending downwardly therefrom, and a plurality of apertures formed in the lower member wherein said apertures are operable and can receive and frictionally engage at least one of the projections extending downwardly from the upper stanchions.

2. An anti-snore dental device comprising:

an upper member having a substantially curved shape and defining an upwardly oriented channel for receiving at least a portion of at least some of the upper teeth of a user, the upper member further defining opposed sides thereof;

a lower member having a substantially curved shaped and defining a downwardly oriented channel for receiving at least a portion of at least some of the lower teeth of a user, the lower member further defining opposed sides thereof;

adjustable connectors for adjustably joining the upper and lower members together wherein the adjustable connectors comprise a pair of lower stanchions each coupled to one of the opposed sides of the lower member, the lower stanchions each having at least two projections extending upwardly therefrom, and a plurality of apertures formed in the upper member wherein said apertures are operable and can receive and frictionally engage at least one of the projections extending upwardly from the upper stanchions.

3. A kit having component parts capable of being assembled into a moldable anti-snore dental device that can be custom fitted by an individual user, the kit comprising:

an upper member having a substantially curved shape and defining an upwardly oriented channel for receiving at least a portion of at least some of the upper teeth of a user, the upper member further defining opposed sides thereof;

a lower member having a substantially curved shaped and defining a downwardly oriented channel for receiving at least a portion of at least some of the lower teeth of a user, the lower member further defining opposed sides thereof;

adjustable connectors for adjustably joining the upper and lower members together wherein the adjustable connectors comprise a pair of upper stanchions each coupled to one of the opposed sides of the upper member, the upper stanchions each having at least two projections extending downwardly therefrom, and a plurality of apertures formed in the lower member wherein said apertures are operable and can receive and frictionally engage at least one of the projections extending downwardly from the upper stanchions, and moldable material for positioning within at least one of the upwardly oriented channel in the upper member, or the downwardly oriented channel in the lower member.

4. A kit according to claim 3 wherein said moldable material is comprised of at least one of the following materials: soft rubber, foam, replaceable wax, moldable resin, ethylene-vinyl acetate copolymer resin, polyether, polysulfide, condensation silicone, hydrophilic addition silicone, light cured elastomer, polyvinylsiloxane material, or hydromonophase vinyl polysiloxane.

5. A kit having component parts capable of being assembled into a moldable anti-snore dental device that can be custom fitted by an individual user, the kit comprising:

an upper member having a substantially curved shape and defining an upwardly oriented channel for receiving at least a portion of at least some of the upper teeth of a user, the upper member further defining opposed sides thereof;

a lower member having a substantially curved shaped and defining a downwardly oriented channel for receiving at least a portion of at least some of the lower teeth of a user, the lower member further defining opposed sides thereof;

adjustable connectors for adjustably joining the upper and lower members together wherein the adjustable connectors comprise a pair of lower stanchions each coupled to one of the opposed sides of the lower member, the lower stanchions each having at least two projections extending upwardly therefrom, and a plurality of apertures formed in the upper member wherein said apertures are operable and can receive and frictionally engage at least one of the projections extending upwardly from the upper stanchions, and moldable material for positioning within at least one of the upwardly oriented channel in the upper member, or the downwardly oriented channel in the lower member.

6. A kit according to claim 5 wherein said moldable material is comprised of at least one of the following materials: soft rubber, foam, replaceable wax, moldable resin, ethylene-vinyl acetate copolymer resin, polyether, polysulfide, condensation silicone, hydrophilic addition silicone, light cured elastomer, polyvinylsiloxane material, or hydromonophase vinyl polysiloxane.

7. An anti-snore dental device comprising:

an upper member having a substantially curved shape and defining an upwardly oriented channel for receiving at least a portion of at least some of the upper teeth of a user, the upper member further defining opposed sides thereof;

a lower member having a substantially curved shaped and defining a downwardly oriented channel for receiving at least a portion of at least some of the lower teeth of a user, the lower member further defining opposed sides thereof;

and, adjustable connectors for adjustably joining the upper and lower members together, and for selectively positioning the lower member relative to the upper member so that when the user's teeth are positioned within the device, the lower jaw of the user is biased substantially forward of its normal resting or biting position to reduce snoring, wherein the adjustable connectors comprise a pair of upper stanchions each coupled to one of the opposed sides of the upper member, the upper stanchions each having a plurality of projections extending downwardly therefrom; and a pair of lower stanchions each coupled to one of the opposed sides of the lower member, the lower stanchions each having a plurality of apertures formed therein, each of the apertures being operable to receive and frictionally engage one of the projections extending downwardly from the upper stanchions.

8. The device of claim 7, wherein each of the projections has a proximal end and a distal end defining a first diameter at the proximal end and a second diameter at the distal end, and further wherein each of the apertures has a top end having a diameter substantially equal to the first diameter and a bottom end having a further diameter substantially equal to the second diameter, wherein the second diameter is substantially slightly greater than the first diameter, whereby the projections may snap into the apertures.

9. The device of claim 7, and further wherein said upper member is adjustably joined to said lower member in a spaced relationship such that there is an anterior tongue space between said upper and lower members.

10. The device of claim 7, and further comprising moldable material positioned within at least one of the channels for substantially conforming to a shape of the teeth.

11. The device of claim 10, wherein the upper and lower members are formed of a first material, and the moldable material is a second material, wherein a softening temperature of the second material is substantially less than a softening temperature of the first material.

12. An anti-snore dental device comprising:

an upper member having a substantially curved shape and defining an upwardly oriented channel for receiving at least a portion of at least some of the upper teeth of a user, the upper member further defining opposed sides thereof;

a lower member having a substantially curved shaped and defining a downwardly oriented channel for receiving at least a portion of at least some of the lower teeth of a user, the lower member further defining opposed sides thereof;

and, adjustable connectors for adjustably joining the upper and lower members together, and for selectively positioning the lower member relative to the upper member so that when the user's teeth are positioned within the device, the lower jaw of the user is biased substantially forward of its normal resting or biting position to reduce snoring, wherein the adjustable connectors comprise a pair of lower stanchions each coupled to one of the opposed sides of the lower member, the lower stanchions each having a plurality of projections extending upwardly therefrom; and a pair of upper stanchions each coupled to one of the opposed sides of the upper member, the upper stanchions each having a plurality of apertures formed therein, each of the apertures being operable to receive and frictionally engage one of the projections extending upwardly from the lower stanchions.

13. The device of claim 12, wherein each of the projections has a proximal end and a distal end defining a first diameter at the proximal end and a second diameter at the distal end, and further wherein each of the apertures has a top end having a diameter substantially equal to the first diameter and a bottom end having a further diameter substantially equal to the second diameter, wherein the second diameter is substantially slightly greater than the first diameter, whereby the projections may snap into the apertures.

14. The device of claim 12, and further wherein said upper member is adjustably joined to said lower member in a spaced relationship such that there is an anterior tongue space between said upper and lower members.

15. The device of claim 12, and further comprising moldable material positioned within at least one of the channels for substantially conforming to a shape of the teeth.

16. The device of claim 15, wherein the upper and lower members are formed of a first material, and the moldable material is a second material, wherein a softening temperature of the second material is substantially less than a softening temperature of the first material.

* * * * *

UNITED STATES PATENT AND TRADEMARK OFFICE
CERTIFICATE OF CORRECTION

PATENT NO. : 5,499,633
DATED : March 19, 1996
INVENTOR(S) : Douglas F. Fenton

It is certified that error appears in the above-indentified patent and that said Letters Patent is hereby corrected as shown below:

Column 1, line 58 of the Patent, change "noctumal" to --nocturnal--.

Column 2, line 45 of the Patent, change "firing" to --fitting--.

Column 5, line 34 of the Patent, change "robber" to --rubber--.

Column 5, line 64 of the Patent, insert --to-- between "device" and "a".

Column 6, line 31 of the Patent, insert --wax-- between "dental" and "sold".

Column 6, line 32 of the Patent, delete "Pink Base Plate Wax" and insert therefor --PINK BASE PLATE WAX--.

UNITED STATES PATENT AND TRADEMARK OFFICE
CERTIFICATE OF CORRECTION

PATENT NO. : 5,499,633

DATED : March 19, 1996

INVENTOR(S) : Douglas F. Fenton

It is certified that error appears in the above-indentified patent and that said Letters Patent is hereby corrected as shown below:

Column 7, line 6 of the Patent, delete "a" between "have" and "an".

Column 7, line 55 of the Patent, insert --to-- between "equal" and "the".

Signed and Sealed this

Nineteenth Day of August, 1997

Attest:

BRUCE LEHMAN

Attesting Officer

Commissioner of Patents and Trademarks